United States Patent [19]

Current

[11] Patent Number: 4,523,029

[45] Date of Patent: Jun. 11, 1985

[54] OXIDATIVE CARBONYLATION OF ALCOHOLS TO PRODUCE DIALKYL OXALATES

[75] Inventor: Steven P. Current, Novato, Calif.

[73] Assignee: Chevron Research Company, San Francisco, Calif.

[21] Appl. No.: 389,209

[22] Filed: Jun. 15, 1982

[51] Int. Cl.$^3$ .............................................. C07C 67/36
[52] U.S. Cl. .................................. 560/204; 502/185; 502/327; 560/190
[58] Field of Search .................... 560/204; 252/466 R; 502/185, 327

[56] References Cited

U.S. PATENT DOCUMENTS

| | | | |
|---|---|---|---|
| 3,393,136 | 7/1968 | Fenton et al. | 560/204 X |
| 3,994,960 | 11/1976 | Yamazaki et al. | 560/204 |
| 4,005,128 | 1/1977 | Zehner et al. | 560/204 |
| 4,005,129 | 1/1977 | Zehner | 560/204 |
| 4,005,130 | 1/1977 | Zehner | 560/204 |
| 4,076,949 | 2/1978 | Zehner | 560/204 |
| 4,118,589 | 10/1978 | Cassar et al. | 560/204 |
| 4,138,587 | 2/1979 | Yamasaki et al. | 560/204 |
| 4,229,591 | 10/1980 | Nishimura et al. | 560/204 |
| 4,230,881 | 10/1980 | Romano et al. | 560/204 |

FOREIGN PATENT DOCUMENTS

| | | |
|---|---|---|
| 2213435 | 10/1973 | Fed. Rep. of Germany . |
| 2514685 | 10/1975 | Fed. Rep. of Germany . |
| 50-157311 | 12/1975 | Japan . |
| 51-29428 | 3/1976 | Japan . |

OTHER PUBLICATIONS

Fenton et al. II, *J. Org. Chem.*, vol. 39, No. 5, (1974), pp. 701–704.

*Primary Examiner*—Natalie Trousof
*Assistant Examiner*—Vera C. Clarke
*Attorney, Agent, or Firm*—S. R. LaPaglia; T. G. DeJonghe; C. J. Caroli

[57] ABSTRACT

A process for the preparation of dialkyl oxalates by the oxidative carbonylation of alcohols which comprises reacting a mixture of carbon monoxide and oxygen with an alcohol in the presence of a heterogeneous catalyst comprising palladium and thallium on carbon.

8 Claims, No Drawings

OXIDATIVE CARBONYLATION OF ALCOHOLS TO PRODUCE DIALKYL OXALATES

BACKGROUND OF THE INVENTION

The present invention is concerned with an improved process for the oxidative carbonylation of alcohols to produce dialkyl oxalates. More particularly, this invention comprises the reaction of a mixture of carbon monoxide and oxygen with an alcohol in the presence of a heterogeneous catalyst comprising palladium and thallium.

The preparation of oxalate esters by the reaction of carbon monoxide and alcohol is well known. U.S. Pat. No. 3,393,136 describes a process for the preparation of oxalates by contacting carbon monoxide at superatmospheric pressure, with a saturated monohydric alcohol solution of a platinum group metal salt and a soluble ferric or cupric salt (redox agent) while maintaining the salts in a highly oxidized state by the simultaneous introduction of oxygen or the application of a direct current electrical potential to the reaction zone. Water scavengers or dehydrating agents such as alkyl orthoformic acid esters must be added to the liquid phase to prevent the accumulation of water.

In an article by Donald F. Fenton and Paul J. Steinwand, *Journal of Organic Chemistry*, Vol. 39, No. 5, 1974, pp. 701–704, a general mechanism for the oxidative carbonylation of alcohols to yield dialkyl oxalates using a palladium redox system, oxygen and dehydrating agents has been proposed. In the absence of the necessary dehydrating agent, a large amount of carbon dioxide is formed and oxalates are not produced. The necessity of the iron or copper redox system during the oxalate synthesis is emphasized. West German Pat. No. 2,213,435 discloses a method for the synthesis of oxalic acid or oxalate esters using water or alcohol, respectively. A platinum group metal salt, a salt of a metal more electropositive than the platinum group metal, e.g. copper (II) chloride, and an alkali metal salt such as lithium chloride comprise the catalyst. Oxygen in stoichiometric amounts was employed as the oxidant. A disadvantage of such reaction is that explosive mixtures of oxygen and carbon monoxide are necessary to effect reaction. Alcohol conversion of less than 5 percent is obtained. Under non-explosive conditions, only trace amounts of oxalate can be obtained.

U.S. Pat. No. 3,994,960 describes a process for the production of dialkyl oxalates by reacting an aliphatic alcohol with CO and oxygen under pressure in the presence of a catalyst of a mixture of a salt of a metal from the platinum group and a salt of copper or iron and a reaction accelerator including nitrates, sulfates, bicarbonates, carbonates, tertiary amines and hydroxides and carboxylates of alkali metals and alkaline earth metals, pyridine, quinoline, urea and thiourea. Conversion of the alcohol employed to the dialkyl oxalates in such a process is low, generally less than 9 mol percent.

In a process similar to that of U.S. Pat. No. 3,994,960 above, West German Offenlegungschrift No. 2,601,139 shows the production of oxalic acid or its alkyl esters by reacting aliphatic alcohols or water with oxygen and carbon monoxide in the presence of palladium salts, redox salts and an amine or ammonia base.

U.S. Pat. Nos. 4,005,128 and 4,005,129 are concerned with the oxidative carbonylation of alcohols with carbon monoxide carried out in the presence of a stoichiometric quantity of a metal oxide such as copper or iron, and a catalytic amount of a metal such as palladium, platinum, copper, etc., and in the presence of an amine or an amine plus an amine salt, respectively.

U.S. Pat. No. 4,005,130 is concerned with a process for the preparation of oxalate esters by the oxidative carbonylation of alcohols with carbon monoxide in the presence of a catalytic amount of copper, nickel, cadmium, cobalt or a zinc metal salt catalyst and at least a stoichiometric amount of an unsubstituted or halogen-substituted 2,5-cyclohexadiene-1,4-dione(1,4-benzoquinone). High yields and selectivity of the oxalate ester, over the carbonate ester and $CO_2$, are obtained and maximized by regulating temperature, carbon monoxide pressure and metal salt catalyst and by maintaining substantially anhydrous conditions.

U.S. Pat. No. 4,076,949 claims a process for the preparation of oxalate esters by reacting an alcohol with a mixture of carbon monoxide and oxygen in the presence of a catalytic mixture of:
  (a) a palladium, rhodium, platinum, copper, or cadmium metal salt compound or mixture thereof;
  (b) an aliphatic, cycloaliphatic, aromatic or heterocyclic amine or ammmonium;
  (c) a copper (I), copper (II), iron (II) or iron (III) oxidant salt compound; and
  (d) an ammonium or substituted ammonium salt compound or acid with a counterion other than a halide. Alternatively, a ligand or coordination complex compound of the metal salt compound may be employed.

U.S. Pat. No. 4,118,589 relates to a process for producing oxalic acid and esters of oxalic acid. More particularly, this patent describes a catalytic process for preparing oxalic acid and esters of same by the oxidative reaction, in a liquid phase, of carbon monoxide and water or alcohols with oxygen in the presence of redox systems. The catalyst systems used in accordance with the teaching of the patent comprise a redox catalyst consisting essentially of a salt of Pd (II) and salts of a metal more electropositive than Pd having at least two oxidation states and, optionally, salts of alkaline metals, and cocatalytic amounts of at least one base having the formula $R_2N$ in which the groups R, which may be like or unlike, are selected from the group consisting of hydrogen and alkyl radicals having from 1 to 10 carbon atoms.

U.S. Pat. No. 4,138,587 describes a process for the preparation of dialkyl oxalates by reacting an aliphatic alcohol with carbon monoxide under pressure in the presence of a catalyst comprising a platinum group metal or a salt thereof, an accelerator composed of one or more compounds selected from the group consisting of nitric acid and nitrogen oxides, and molecular oxygen.

U.S. Pat. No. 4,230,881 discloses a method for preparing esters of oxalic acid by the reaction of carbon monoxide and an alcohol in the presence of a catalyst consisting of a complex of palladium and a co-catalyst consisting of a compound having acidic properties selected from the group consisting of amine salts, carboxylic acids, phenol, succinimide and phthalimide.

Commonly assigned U.S. Pat. No. 4,281,174 is concerned with a process for the preparation of dialkyl oxalates by the oxidative carbonylation of alcohols which comprises reacting a mixture of carbon monoxide and oxygen with an alcohol in the presence of a catalytic amount of a catalyst comprising palladium in complex combination with a ligand, a quinone and a redox agent.

The liquid oxalate esters are solvents, but the preferred use is as feedstock for hydrogenation to ethylene glycol. The oxalate esters can also be hydrolyzed to oxalic acid which has a number of industrial uses.

SUMMARY OF THE INVENTION

The present invention provides a superior process for the production of dialkyl oxalates by the oxidative carbonylation of an aliphatic alcohol with a mixture of carbon monoxide and oxygen in the presence of a heterogeneous catalyst comprising palladium and thallium on carbon. Mild reaction conditions of temperature and pressure effective to cause reaction of the alcohol and carbon monoxide to produce dialkyl oxalates are employed.

Among other factors, the present invention is based on the discovery that the production of dialkyl oxalates in high yields and better selectivity is effected by carrying out the reaction of alcohol and carbon monoxide admixed with oxygen in the presence of a heterogeneous catalyst comprising palladium and thallium on carbon at a reaction temperature below about 100° C. and above about 30° C. and a reaction pressure below about 1500 psi and above about 500 psi.

DETAILED DESCRIPTION OF THE INVENTION

As hereinbefore mentioned, the present invention is based on the discovery that superior yields of dialkyl oxalates at better selectivities can be obtained from the reaction of an alcohol and a mixture of carbon monoxide, oxygen or oxygen-containing gas, such as air, in the presence of a heterogeneous catalyst comprising palladium and thallium on carbon. Reaction conditions of pressure, and particularly temperature, are less severe than those encountered in the prior art. Substantial quantities of soluble co-catalysts, redox agents, accelerators, and the like are not required. In addition, the reaction may be effectively carried out even in the presence of water and thus dehydrating agents are not needed to maintain high selectivity. Pursuant to the invention, a minimum amount of by-product carbonate is formed, and selectivities of the order of 90 to 100 mol percent dialkyl oxylate can be obtained.

The alcohols suitable for use in the process of the present invention and generally employed in at least stoichiometric quantities are aliphatic alcohols, or alkanols, having from 1 to 6 carbon atoms such as methanol, ethanol, n-propanol, isopropanol, n-butanol, isobutanol, n-amyl alcohol, isoamyl alcohol, n-hexanol, and isohexanol.

The reaction may be carried out in an autoclave or any other high pressure reactor. A general procedure is to charge the alcohol and catalyst mixture into the reactor vessel, introduce the proper amount of carbon monoxide and oxygen to obtain the desired reaction pressure and then heat the mixture at the desired temperature for the appropriate period. The reaction can be carried out batchwise or as a continuous process and the order of addition of the reactants may be varied to suit the particular apparatus employed. The reaction products are recovered and treated by any conventional method such as distillation, crystallization, and/or filtration, etc., to effect separation of the oxalate from unreacted materials, catalysts, by-products, etc. Initially the reaction is performed under relatively anhydrous conditions, but water is produced during the course of the reaction.

Generally, the proportions of the catalyst components used in the reaction will be equivalent to between about 0.05 to 2, preferably 0.1 to 1 mol of palladium per mol of thallium.

The reaction of the present invention may be carried out with or without a solvent. Although not required, solvents, if desired, which are chemically inert to the components of the reaction system may be employed. Suitable solvents include, for example, hydrocarbons such as hexane, heptane, octane, toluene and xylene; ethers such as tetrahydrofuran and diethylether; halogenated hydrocarbons such as methylene chloride, chloroform and dichlorobenzene; organic esters or diesters such as ethyl acetate, n-propyl formate, isopropyl acetate, sec- and isobutyl acetate, amyl acetate, cyclohexyl acetate, n-propyl benzoate, and lower alkyl phthalates; and nitriles such as acetonitrile. The preferred method of operation is with excess alcohol used with the carbonylation reaction, functioning also as a solvent.

As indicated above, the reaction can be suitably performed by introducing the carbon monoxide and oxygen at a desired pressure into contact with the alcoholic reaction medium containing the specified alcohol and catalyst mixture and heating to the desired temperature. In general, carbon monoxide pressures of about 500 psi to about 1500 psi, preferably 750 to 1250 psi, may be employed. Excess quantities of carbon monoxide are generally employed. A suitable recycle of the carbon monoxide may be employed.

The reaction will proceed at a temperature above about 30° C. and below about 100° C. It is generally preferred to operate the process at temperatures in the range of about 30° C. to about 60° C., more preferably between about 40° C. and 55° C., in order to obtain maximum selectivity. Heating and/or cooling means may be employed interior and/or exterior of the reaction to maintain the temperature within the desired range.

At least stoichiometric amounts of oxygen or an oxygen-containing gas such as air are employed, the oxygen partial pressure being such as to avoid an explosive mixture. In accordance with the *Handbook of Chemistry and Physics,* 48th Edition, 1967, the explosive limit of pure oxygen in carbon monoxide is 6.1 to 84.5 volume percent and air in carbon monoxide is 25.8 to 87.5 volume percent. The volume percent of the oxygen in the oxygen-carbon monoxide mixture usually amounts to 3 to 6 percent. In carrying out the reaction, the oxygen is charged to the reaction vessel to the desired pressure and concentration and for safety reasons, may be charged in portions.

The reaction time is generally dependent upon the alcohol being reacted, temperature, pressure and on the amount of catalyst being charged as well as the type of equipment being employed. Reaction times will vary dependent on whether the process is continuous or batch. The reaction is limited by the available alcohol, carbon monoxide, and oxygen.

The following examples are provided to illustrate the invention in accordance with the principles of this invention but are not to be construed as limiting the invention in any way except as indicated by the appended claims.

EXAMPLES

Example 1

A palladium-thallium on carbon catalyst was prepared by impregnating 20.0 grams of activated carbon with a solution of 2.20 grams of thallium (III) nitrate in 20.0 mls water followed by heating under a flow of nitrogen at 100° C. for 1 hour and 250° C. for 6 hours. The resultant material was further impregnated with a solution of 0.501 grams tetramminepalladium (II) nitrate in 20.0 mls water, again followed by heating under a flow of nitrogen at 100° C. for 1 hour and 250° C. for 6 hours.

Example 2

A palladium-thallium on carbon catalyst was prepared by dissolving 0.131 grams of tetramminepalladium (II) nitrate and 0.345 grams of thallium (III) nitrate in 5.0 mls of a mixture of equal volumes of 70 percent nitric acid and water. This solution was used to impregnate 5.0 grams of activated carbon powder which was then dried at 80° C. for 2 hours and then calcined at 250° C. for 4 hours under a flow of nitrogen.

Example 3

A 300-ml, stainless steel autoclave was flushed with nitrogen and charged with 150 mls methanol, 1.35 grams diglyme, and 5.32 grams of the palladium-thallium on carbon catalyst described in Example 1. The reactor was further charged with 1250 psi carbon monoxide followed by 75 psi oxygen. The reaction mixture was stirred at 1600 rpm and heated to 50° C. Liquid samples were removed periodically and analyzed by gas chromatography. The time required for the reactor to reach 50° C. is defined as zero hours. For each 30 mmols of product formed, an additional 100 psi of carbon monoxide and 25 psi of oxygen were added to the reactor, the results are shown in Table 1.

TABLE 1

| | Palladium-Thallium on Carbon at 50° C. | | | |
|---|---|---|---|---|
| | Products, mmol/mmol Pd | | | |
| Time, hrs. | Dimethyl Oxalate | Dimethyl Carbonate | Methyl Formate | Methylal |
| 0 | 9.2 | 0 | 0 | 0 |
| 1.5 | 75.9 | 0.4 | 0 | 0 |
| 4.0 | 144.3 | 2.9 | 0 | 0 |
| 8.0 | 203.6 | 4.5 | 0 | 1.2 |
| 12.0 | 229.4 | 5.3 | 5.1 | 5.3 |

Example 4

Two small stainless steel reactors were each charged with 3.0 mls methanol and 0.106 gram of the palladium-thallium on carbon catalyst described in Example 1. Each was further charged with 750 psi of carbon monoxide and 250 psi of air. One reactor was heated at 50° C. and one at 80° C. with gentle shaking for 4 hours. Each was cooled, gases vented, and 0.050 ml diglyme added to serve as a standard for gas chromatographic analysis. The results are shown in Table 2.

TABLE 2

| | Products, mmol/mmol Pd | |
|---|---|---|
| Temperature | Dimethyl Oxalate | Dimethyl Carbonate |
| 50° C. | 33.7 | 0 |
| 80° C. | 32.6 | 8.7 |

Example 5

A 300-ml, stainless steel autoclave was flushed with nitrogen and charged with 100 mls methanol, 1.34 grams diglyme, and 2.47 grams of the palladium-thallium catalyst described in Example 2. The reactor was further charged with 1250 psi of carbon monoxide and 75 psi of oxygen. The reaction mixture was stirred and heated to 90° C. Time zero is defined as the time when the reaction reached 90° C. Liquid samples were removed periodically and analyzed for gas chromatography. For each 30 mmols of products formed, an additional 100 psi of carbon monoxide and 25 psi of oxygen was added to the reactor. The results are shown in Table 3.

TABLE 3

| | Palladium-Thallium on Carbon at 90° C. | | | |
|---|---|---|---|---|
| | Products, mmol/mmol Pd | | | |
| Time, hrs. | Dimethyl Oxalate | Dimethyl Carbonate | Methyl Formate | Methylal |
| 0 | 45.4 | 2.2 | 0 | 0 |
| 1.5 | 93.9 | 12.4 | 0 | 3.4 |
| 3.0 | 111.6 | 16.9 | 0 | 20.7 |
| 7.0 | 142.9 | 25.9 | 6.6 | 75.3 |
| 11.0 | 165.7 | 34.6 | 12.6 | 141.9 |

What is claimed is:

1. A process for the preparation of dialkyl oxalates by the oxidative carbonylation reaction which comprises reacting an alkanol having from 1 to 6 carbon atoms with a mixture of carbon monoxide and oxygen in the presence of a heterogeneous catalyst comprising palladium and thallium on carbon at a temperature between about 30° C. and 100° C. and a carbon monoxide partial pressure in the range of about 500 psi to 1500 psi.

2. The process according to claim 1, wherein the reaction temperature is between about 30° C. and 60° C.

3. The process according to claim 1, wherein the reaction temperature is between about 40° C. and 55° C.

4. The process according to claim 1, wherein the carbon monoxide partial pressure is in the range of about 750 psi to 1250 psi.

5. The process according to claim 1, wherein the palladium and thallium are present in molar ratios of about 0.05 to 2 mols of palladium per mol of thallium.

6. The process according to claim 1, wherein the palladium and thallium are present in molar ratios of about 0.1 to 1 mol of palladium per mol of thallium.

7. The process according to claim 1, wherein the reaction is carried out in the presence of water.

8. The process according to claim 1, wherein the reaction is carried out in the presence of a solvent inert to the components of the reaction system.

* * * * *